United States Patent
Joswig et al.

(10) Patent No.: US 6,260,416 B1
(45) Date of Patent: *Jul. 17, 2001

(54) DEVICE FOR MEASURING AND/OR DETECTING THE INTERNAL PRESSURE OF LUMENS OF FLEXIBLE TUBES

(75) Inventors: Jurgen Joswig; Jens Oswald; Steffen Seifert, all of Dresden (DE)

(73) Assignee: Forderverein Institut fur Medizintechnik Dresden E.V. (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/147,587
(22) PCT Filed: May 28, 1998
(86) PCT No.: PCT/DE98/01463
§ 371 Date: Jan. 28, 1999
§ 102(e) Date: Jan. 28, 1999
(87) PCT Pub. No.: WO98/54555
PCT Pub. Date: Dec. 3, 1998

(30) Foreign Application Priority Data

May 28, 1997 (DE) .............................................. 197 22 555

(51) Int. Cl.[7] .................. G01L 7/00; G01L 1/26
(52) U.S. Cl. ......................................... 73/714; 73/862.391
(58) Field of Search ....................... 73/862.391, 862.454, 73/862.471, 862.581, 862.582, 862.583, 862.584, 862.636, 862.637, 862.642, 700, 724, 727, 714, 862.451, 862.392, 118.1, 119 A

(56) References Cited

U.S. PATENT DOCUMENTS 3,327,526    6/1967    North .
4,807,479    * 2/1989    Sako et al. .............................. 73/730

FOREIGN PATENT DOCUMENTS

| 24 40 493 | 7/1975 | (DE) . |
| 0 126 033 | 11/1984 | (EP) . |
| 0 378 312 | 7/1990 | (EP) . |
| 2 019 581 | 10/1979 | (GB) . |
| 2 180 651 | 4/1987 | (GB) . |

* cited by examiner

Primary Examiner—Benjamin H. Fuller
Assistant Examiner—Abdullahi Aw-Musse
(74) Attorney, Agent, or Firm—Hoffman, Wasson & Gitler

(57) ABSTRACT

The invention relates to a device for measuring and/or detecting the internal pressure of lumens or flexible tubes. The inventive device has a cage which surrounds the outer wall of the lumen or the tube, and at least one sensor for measuring the force exerted on said cage by the internal pressure.

17 Claims, 1 Drawing Sheet

DEVICE FOR MEASURING AND/OR DETECTING THE INTERNAL PRESSURE OF LUMENS OF FLEXIBLE TUBES

BACKGROUND OF THE INVENTION

For measuring the interior pressure of hoses or lumen, pressure sensors that directly impinged with or submitted to the interior pressure are known. The disadvantage of this prior art is that the medium being transported through the respective lumen or hose comes into direct contact with parts of the sensor and that the channel formed by the hose must be opened in order to connect the sensor.

The object of the invention is to present a new device that enables the simplified measuring of pressure without opening the hose or lumen.

SUMMARY OF THE INVENTION

Measuring interior pressure is to be understood according to invention among other things as the measuring with production of an analog or digital variable signal dependent on the pressure, but among other things also verification and monitoring of the interior pressure, of changes in pressure and/or of the upper and/or lower deviation from pressure values (threshold values).

The measuring and/or determination and/or acquisition of the interior pressure or of the pressure change in a hose or lumen occurs by measuring and/or acquisition of the force which the interior pressure exerts on the retainer or cage surrounding the hose. The hose or lumen is enclosed in this retainer in such a way that a deformation or change in shape of the lumen or hose or of the wall of these does not occur. For this purpose the retainer is preferably formed or adjusted in such a way that he wall of the hose or lumen is supported by the retainer for example without deformation, i.e. also especially without interior tensile stress that would stretch the material in the case of a lumen or hose with no pressure or with a low interior pressure, but also with the highest expected pressure.

The inherent elasticity of the material of the hose or lumen is insignificant for the invention, so that measuring and/or determination and/or acquisition of the interior pressure is also possible with hoses made of inflexible material, for example with an elastic-viscous hose material. Especially also changes in the elasticity of the respective hose, for example through aging etc. have no effect on the measuring result.

BRIEF DESCRIPTION OP THE INVENTION

Figure 1:
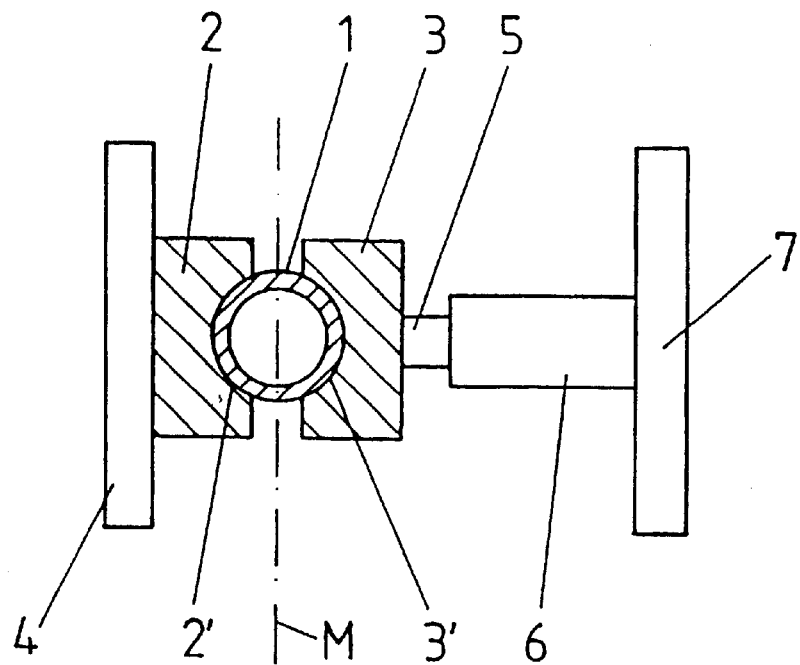
Figure 2:
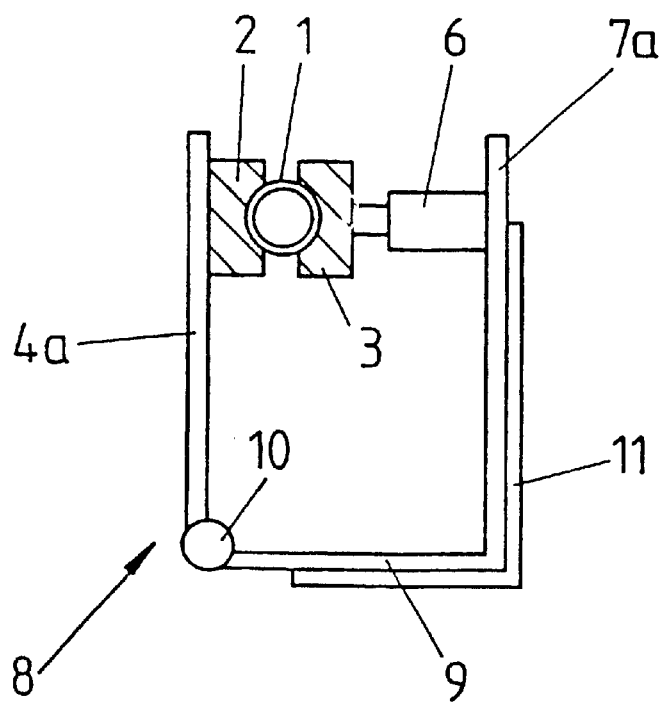

Examples of the invention are now described in more detail in connection with the Figures, which illustrate:

FIG. 1 in a very simplified depiction, a cross section of a hose as well as of a first embodiment of the device according to invention FIG. 2 a similar depiction as in FIG. 1, however in a second possible embodiment of the invention

DETAILED DESCRIPTION OF THE INVENTION

In the figures, a lumen or a hose 1 is impinged with interior pressure P or with the pressure of a medium located within, or flowing through, the hose. The device illustrated in FIG. 1 serves to measure the interior pressure P or the pressure change ΔP. It consists of two saucer-type or grooved bearing elements 2, 3, which hold the hose 1 between them and form an almost completely inflexible retainer surrounding the hose. The two bearing elements 2, 3 are symmetrically arranged with a vertical middle plane M. Bearing element 2 is directly connected to a fixed thrust bearing 4. Bearing element 3 is supported on its opposite side on the hose 1 by a thrust bearing 7 over an adjusting element 5 and a force sensor 6. The bearing elements 2, 3 form a circular cylindrical arched concave bearing surface 2' or 3', respectively, for the external surface of the hose 1. With the adjusting element 5, which enables an axial adjustment perpendicular to the plane of the thrust bearing 7, the bearing element 3 can be advanced so that it fits with its circular arc concave bearing surface 3' flat and tightly against the outer wall of the non-stretched hose 1.

If the interior of the hose 1 is impinged with the pressure P or if a change in the pressure P occurs, this pressure change ΔP will be converted by the power sensor 6 into an electrical signal. The magnitude or value of the signal is a measure of the pressure P or the pressure change ΔP. The power sensor 6 is preferably a sensor that already delivers a measuring signal for minimal mechanical changes, for example a sensor based on the piezo effect, a sensor with a variable electrical resistance dependent on the pressure, with a variable capacity dependent on the measured pressure or power, an optoelectrical sensor and so on. Also, a switch that changes over from a first state into a second state when the pressure P or the pressure change ΔP exceeds a pre-defined threshold value is suitable as a power sensor.

The device shown in FIG. 2 differs from the device in FIG. 1 principally in that the two thrust bearings 4 and 7 are formed by the flanks 4a and 7a of a U-shaped or bow-shaped frame 8. In addition to the flanks 4a and 7a the frame has, a yoke 9 connecting the two flanks. The flank 4a is coupled to the yoke 9 (joint 10) and can be swiveled on an axis parallel to the axis of hose 1 toward the outside, for the purpose of inserting and removing the hose 1 into or from the space between the bearing elements 2 and 3. By means of a locking device not shown the joint 10 can be locked and/or the two free ends of the flanks 4a and 7a can be connected to each other, so that a closed, fixed frame 8 is attained. With the outer surface of flank 7a and yoke 9, the frame 8 fits onto an elbow support or bracket 11 to which it is suitably fastened. Bracket 11 is part of a device or device support etc. not further depicted.

The devices described here are suitable for measuring and/or monitoring and/or determination and/or acquisition of the interior pressure of hoses or other lumen that convey a fluid, gaseous or vaporous medium. For example, for measuring and/or acquisition, and monitoring the interior hose pressure in or of medical equipment, but of other equipment as well. Especially the pressure of aggressive or poisonous media can also be measured and/or acquired with the devices. Furthermore, the measuring of blood pressure of blood vessels that are not open is possible. A special advantage lies in the fact that the measurement and/or acquisition of pressure can occur with no great risk with sterile systems, since a measuring head that is directly in contact with the interior of the respective lumen or hose 1 is not necessary.

The adjustment of the two bearing elements 2 and 3 relative to each other occurs in such as way that the bearing elements 2 and 3 for example fit tightly against the hose when not under pressure. The hose 1 between the bearing elements 2 and 3 is possibly even slightly pressed together so that upon impingement of the hose 1 with the interior pressure P the resulting force from the interior pressure P on the power sensor can be measured, without deformation or stretching of the wall of the section of hose located between the bearing elements 2 and 3.

If the flow resistance for the fluid, gaseous or vaporous medium flowing through hose 1 is known, then the flow volume can be determined from the measured pressure P.

The invention was described above using examples. Of course, numerous alterations and modifications are possible without abandoning the object of invention upon which the invention is based.

| List of Reference Marks | |
|---|---|
| 1 | hose/lumen |
| 2, 3 | bearing element |
| 4 | thrust bearing |
| 4a | flank or shank |
| 5 | adjusting element |
| 6 | power sensor |
| 7 | thrust bearing |
| 7a | flank or shank |
| 8 | frame |
| 9 | yoke |
| 10 | joint |
| 11 | bracket |

What is claimed is:

1. Device for monitoring the interior pressure of a hose within a pressure range comprising:
    a non-flexible retainer having a first and a second piece each providing a bearing surface for at least partly surrounding the hose wall and tightly fitting against the outer surface of the hose wall of the non-stretch hose, and
        a sensor connected to the retainer for measuring the force exerted by the interior pressure on the retainer,
    said hose being between the first and a second piece of the retainer so that deformation of the hose wall does not occur by the interior pressure within the pressure range, and
    said sensor being responsive to the force acting in between the first and the second piece of the retainer.

2. The device of claim 1, wherein the retainer has a first and a second piece.

3. The device of claim 2, wherein the sensor measures the force between the first and second piece of the retainer.

4. The device of claim 1, wherein the retainer is attached to a thrust bearing.

5. The device of claim 4, wherein the sensor measures the force between the retainer and said thrust bearing.

6. The device of claim 4, wherein the thrust bearing are flanks of a U-shaped frame.

7. The device of claim 6, wherein the flanks are pivotally connected to one another.

8. The device of claim 7, wherein the flanks are lockable.

9. The device of claim 4, further comprising an adjustment element between the retainer and thrust bearing to position the retainer over the hose.

10. The device of claim 1, wherein the sensor has a first state and a second state, the sensor switching from the first state to the second state when a predefined value is reached.

11. Device for monitoring the interior pressure of a hose within a pressure range, comprising:
    a non-flexible retainer with a first and a second piece each providing a bearing surface for partly surrounding the hose on a hose wall and for flat and tightly fitting against the outer surface of the house wall of the non-stretched hose, and
    a sensor connected to the retainer for measuring the force exerted by the interior pressure on the retainer,
    said hose being enclosed in-between the first and a second piece of the retainer in such that a deformation of the hose wall does not occur by the interior pressure within the pressure range, and
    said sensor being responsive to the force acting in between the first and the second piece of the retainer.

12. A device for monitoring the interior pressure of a hose so that deformation of the hose wall does not occur by the interior pressure comprising:
    a first bearing element,
    a first thrust bearing connected to said first bearing element,
    a second bearing element,
    a second thrust bearing element connected to said second bearing element,
    said first and second bearing element-forming an inflexible retainer for retaining a hose, and
    a force sensor attached to said second thrust bearing for measure a pressure change in the hose.

13. The device of claim 12, further comprising an adjustment element between said second thrust bearing and said force sensor for axially adjusting the position of said second bearing element.

14. The device of claim 12, wherein said force sensor is based on the piezo effect.

15. The device of claim 12, wherein said force sensor has a variable electrical resistance dependent on pressure.

16. The device of claim 12, wherein said first and second thrust bearings are flanks of a U-shaped frame.

17. The device of claim 16, further comprising a yoke connecting said first and second thrust bearings.

\* \* \* \* \*